United States Patent [19]

Lewellyn

[11] Patent Number: 4,482,500

[45] Date of Patent: Nov. 13, 1984

[54] PROCESS FOR THE PREPARATION OF N-ALLYL-O-ALKYL THIONOCARBAMATES

[75] Inventor: Morris E. Lewellyn, Bridgeport, Conn.

[73] Assignee: American Cyanamid Company, Stamford, Conn.

[21] Appl. No.: 410,689

[22] Filed: Aug. 23, 1982

[51] Int. Cl.³ .......................................... C07C 155/02
[52] U.S. Cl. ................................................ 260/455 A
[58] Field of Search ................................... 260/455 A

[56] References Cited

U.S. PATENT DOCUMENTS 2,462,433 11/1963 Searles ............................ 260/455 A Primary Examiner—Henry R. Jiles
Assistant Examiner—Robert C. Whittenbaugh
Attorney, Agent, or Firm—John W. Cornell

[57] ABSTRACT

A process for the preparation of N-allyl-O-alkyl thionocarbamates is disclosed which comprises reacting in an aqueous solvent and in the presence of a phase transfer catalyst a cyanide salt, sulfur and an allyl halide to form an allyl isothiocyanate and then reacting said allyl isothiocyanate in the presence of certain catalysts with an alcohol.

17 Claims, No Drawings

PROCESS FOR THE PREPARATION OF N-ALLYL-O-ALKYL THIONOCARBAMATES

The present invention relates to a simple and efficient process for the preparation of N-allyl-O-alkyl thionocarbamates which are useful promoters for sulfide ore flotation, as described in a commonly assigned, copending application, Ser. No. 06/309,851, filed Oct. 8, 1981.

BACKGROUND OF THE INVENTION

The preparation of organic isothiocyanates and thiocyanates by the reaction of a reactive organic halide, sulfur and an alkali metal cyanide in an oxygenated organic solvent, such as an aliphatic alcohol or ketone, was reported by Searles, U.S. Pat. No. 2,462,433. The Searles process suffers from several disadvantages:
1. Removal of salt from the organic reaction mixture,
2. Removal of solvent from the product, and
3. Distillation of the desired organic isothiocyanate from the co-produced organic thiocyanate.

When an alcoholic solvent is used in the Searles process and the salt is not removed following formation of the organic isothiocyanate, low yields of thioncarbamate are obtained in the subsequent reaction with an alcohol.

The further reaction of an organic isothiocyanate with an aliphatic alcohol under the influence of a suitable catalyst, such as ferric acetylacetonate or dibutyl tin dilaurate, is known and is described by Iwakura et al, Can. J. Chem. 40, 2369-2375 (1962).

Reeves et al, Synthetic Communications 6 (7), 509-514 (1976), disclose that the reaction of an alkyl halide with aqueous potassium thiocyanate under the influence of a phase transfer catalyst (quaternary ammonium halides) or n-butylamine or tri-n-butylamine, affords alkyl thiocyanates. When allyl halides were used, a mixture of allyl thiocyanate and allyl isothiocyanate was obtained, which requires distillation to recover the desired isothiocyanate.

Generally, the prior art processes provide many disadvantages, including the complicated removal of reaction solvent and unwanted reaction products, exposure to irritating intermediate and deficient yields. These and other deficiencies of the prior art processes are overcome by the process of the instant invention which provides for a process for the preparation of N-allyl-O-alkyl thionocarbamates which comprises:
  (a) reacting in the presence of a phase transfer catalyst, an alkali metal or ammonium cyanide, sulfur, and an allyl halide in water as the reaction solvent to produce a reaction mixture comprising an organic phase containing an allyl isothiocyanate and an aqueous phase;
  (b) separating said aqueous phase from said organic phase; and
  (c) reacting said allyl isothiocyanate with an alcohol in the presence of a urethane catalyst to produce the N-allyl-O-alkyl thionocarbamate.

The present invention provides many improvements over the prior art disclosed processes in that (1) water is used as a solvent for the preparation of the allyl isothiocyanate, (2) the alkali metal or ammonium thiocyanate solution is readily prepared in situ by the use of a phase transfer catalyst, which additionally provides high yields of the allyl isothiocyanate without distillation, (3) salt formed in the reaction is readily removed, (4) the allyl isothiocyanate need not be isolated from the reaction vessel in which it is prepared, thus eliminating the need for handling an irritating lacrymator, and (5) the preparation of the N-allyl-O-alkyl thionocarbamate is readily prepared in high yields by the addition of an aliphatic alcohol to the allyl isothiocyanate and reaction under the influence of a suitable catalyst. These and other advantages of the instant process will become more evident in the detailed disclosure that follows.

DETAILED DESCRIPTION OF THE INVENTION

Applicants have discovered a process whereby an aqueous solution of an alkali metal or ammonium cyanide compound is reacted with a slight excess of sulfur in the presence of a phase transfer catalyst (PTC) to provide an aqueous solution of an alkali metal or ammonium thiocyanate, which is then reacted with an allyl or substituted allyl halide and heated to reflux to produce an allyl or substituted allyl isothiocyanate and an aqueous solution of salt. The two phases are separated and the allyl or substituted allyl isothiocyanate is then reacted with an aliphatic alcohol in the presence of a suitable catalyst at an elevated temperature to provide the desired product.

The overall chemistry of the process of the invention is illustrated below:

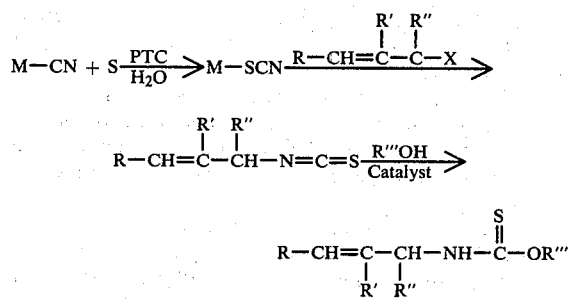

where M represents an alkali metal or $NH_4^+$, X represents a halide atom, and R, R', R" are hydrogen, alkyl or aryl, and R''' is alkyl. The instant process is particularly amenable to situations wherein when R, R' and R" are alkyl the alkyl group is a lower alkyl of 1 to 4 carbons and wherein R''' is an alkyl of 1 to 8 carbons.

The first step of the instant process comprises reacting in the presence of a phase transfer catalyst, an alkali metal or ammonium cyanide, sulfur and an allyl halide in water as the reaction solvent to produce a reaction mixture comprising an organic phase containing an allyl isothiocyanate and an aqueous phase. While the undertaking of this first step is subject to variations of technique, it preferably comprises the following protocol:
  (a) forming an aqueous solution of said alkali metal or ammonium thiocyanate by the addition of about 0.5 to about 1.0 stoichrometic percent excess of said sulfur to an aqueous solution of said alkali metal or ammonium cyanide where said phase transfer catalyst is present in the amount of about 0.05 to 4 mole percent based on said alkali metal or ammonium cyanide;
  (b) adding to said thiocyanate solution at a temperature of less than about 40° C., about a 1.0 to 1.1 molar proportion based on said alkali metal or ammonium cyanide of allyl halide; and (c) heating the resulting reaction mixture at reflux for a period of time sufficient to achieve a ratio of allyl isothiocyanate to allylthiocyanate of at least 8.5:1.

When sulfur reacts with an alkali metal cyanide, an exotherm is produced (16–18 Kcal/mole with sodium cyanide). In this reaction an aqueous solution containing 35–40 percent alkali metal or ammonium cyanide is formed, to which is added a phase transfer catalyst, followed by the portionwise addition of a slight stoichiometric excess of sulfur.

Phase transfer catalysts have been used for many nucleophilic substituted reactions. The technique involves the use of an organic cationic species which can act to transfer a nucleophilic anion from the aqueous phase into the organic phase where it can react.

In theory, any phase transfer catalyst can be used in the practice of the present invention. Preferably, the phase transfer catalysts are tetraalkyl ammonium halides and tetraalkyl phosphonium halides. Useful compounds are those in which, broadly, the alkyl groups may contain from 1 to 20 carbon atoms and a total carbon content of up to about 40 carbon atoms. Preferably, the alkyl groups will contain from 1 to 10 carbon atoms and a total carbon content of about 16 to about 22 carbon atoms. Especially preferred species are tetra-n-butyl ammonium chloride and octyldecyl dimethyl ammonium chloride. Other useful catalysts include, but are not limited to, tallow trimethylammonium chloride, dodecyltrimethylammonium chloride, ditallowdimethylammonium chloride, hexadecyltrimethylammonium chloride, dicocodimethylammonium chloride, and the like.

In general, the phase transfer catalyst is used in the process in an amount of from about 0.05 to 4 mole percent, based on the alkali metal or ammonium cyanide used. Preferably, the catalyst usage is 0.1 to about 1.0 mole percent.

Sulfur is added portionwise to the aqueous solution of alkali metal or ammonium cyanide and phase transfer catalyst over a period of time, with external cooling to maintain the temperature, which rises rapidly to about 110° C., in the range of about 60°–80° C. and a slight excess of sulfur over that amount stoichiometrically required is preferably used to assure that the aqueous phase contains a low cyanide content following completion of the reaction. Generally, an excess of 0.5 to 1.0 mole percent used in the amide salt is sufficient. If greater than about one percent excess is used, difficulty is encountered in separating the phases in the subsequent reaction.

Following the addition of the sulfur, the thiocyanate solution is cooled to a suitable temperature, for example, below 40° C., and an allyl or substituted allyl halide is added rapidly. The allyl halide may be used in any reasonable amount; it is preferable to use an amount ranging from about 1.0 to about 1.1 moles per mole of thiocyanate, and more desirably about 1.05 to 1.1 moles. It has been observed that a slight excess of the allyl halide provides higher yields and reduced reaction times.

Although the present invention will be particularly illustrated with reference to N-allyl- and N-methyallyl-O-alkyl thionocarbamates, it will be understood that the invention is also applicable to various allyl compounds including, but not limited to, substituted allyl compounds, such as $C_1$ to $C_4$ alkyl substituted allyl and aryl substituted allyl derivatives, represented by the formula:

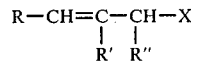

wherein R, R' and R" are hydrogen, $C_1$–$C_4$ alkyl or aryl, for example, N-crotyl and N-cinnamyl. Allyl halides wherein the halide moiety is Cl, Br, or I are preferred reactants, especially the chlorides. Other compounds which may be used include the tosylate and mesylate or any other good leaving group. Such compounds include allyl chloride, allyl bromide, allyl iodide, methallyl chloride, methallyl bromide, methallyl iodide, allyl tosylate, allyl mesylate, methallyl tosylate, methallyl mesylate, and the like.

The reaction mixture is then slowly heated to reflux (90°–95° C.) and a gentle reflux is maintained for about 3 to 5 hours. The resulting alkali metal or ammonium thiocyanate reaction mixture will comprise an organic phase and aqueous phase the mixture preferably having a thiocyanate concentration of about 50 percent.

The second step of the instant process comprises separating the aqueous phase from the organic phase. While the undertaking of this second step is subject to variations of technique it preferably comprises the following protocol:

(a) adding water to the reaction mixture to dissolve salt formed in the reaction;

(b) separating the aqueous phase from the organic phase; and (c) removing unreacted allyl halide and trace amounts of water from said organic phase by heating said phase in vacuo for a time, temperature, and vacuum sufficient to remove unreacted allyl halide and trace water.

It is important that the water content of the subsequent reaction of the allyl isothiocyanate and aliphatic alcohol be as low as possible to preclude problems with hydrolysis of the catalysts to be used therein. In general, the water content of this reaction should be below about 0.25%. Therefore, it is desirable to remove as much residual water from the allyl isothiocyanate as possible.

The third step of the instant invention comprises reacting the allyl isothiocyanate as produced above with an alcohol in the presence of a urethane catalyst to produce the N-allyl-O-alkyl thionocarbamate. While the undertaking of this third step is subject to variations of technique, it preferably comprises the following protocol:

(a) adding to said organic phase containing said allyl isothiocyanate about 1 to about 2 molar proportions based on said allyl isothiocyanate of a linear or branched chain primary alcohol and from about 0.1 to 4 mole percent based on said allyl isothiocyanate of a urethane catalyst; and (b) heating the resulting mixture to a temperature sufficient and for a time sufficient to convert said allyl isothiocyanate to N-allyl-O-alkyl thionocarbamate.

In general, it is preferred that the urethane catalyst be selected from the group consisting of tetraalkyl titanates, tetraalkyl zirconates, metal acetylacetonates, and dialkyl tin dicarboxylates.

A particular advantage of the instant invention is that the allyl isothiocyanate need not be isolated from the vessel in which it is produced. Therefore, an aliphatic alcohol is merely added thereto, along with a suitable catalyst. The reaction mixture may then be heated to a temperature and period sufficient to complete the formation of the N-allyl-O-alkyl thionocarbamates. General temperatures of about 100° C. to 120° C. are suitable with about 110° C. to 120° C. being preferred. Heating to these temperatures for a period of about 3 to 6 hours generally will be sufficient. Any excess alcohol may then be removed, preferably by application of a vacuum and yields of the product in excess of 85 percent have been experienced.

While various aliphatic alcohols may be employed depending on the desired end product, the instant process is particularly amenable to aliphatic alcohols which are $C_1$ to $C_8$ linear or branched chain primary alcohols, preferably $C_1$ to $C_5$ primary alcohols, and especially $C_3$ and $C_4$ primary alcohols. The aliphatic chain may be interrupted by a hetero atom, such as —O—, —S—, or —NH—. Examples of such alcohols include methanol, ethanol, n-propanol, n-butanol, isobutanol, n-amyl alcohol, isoamyl alcohol, n-hexanol, n-octanol, 2-methoxyethanol, 2-ethoxyethanol, 2-(methylamino)ethanol, 2-(methylthio)ethanol, and the like. Products may also be obtained using butyl carbitol, methyl cellosolve, Carbowax 200, methyl carbitol, diethylene glycol, triethylene glycol, Carbowax 400, Carbowax 600, and the like.

The amount of aliphatic alcohol used in the reaction to produce the N-allyl-O-alkyl thionocarbamate in general will range from about equimolar up to about 100 percent molar excess, based on the alkali metal cyanide charged in the initial reaction. It is preferred to utilize as close to an equimolar amount of alcohol as possible to avoid the necessity of having to remove and recover the excess.

A suitable catalyst for the reaction is added to the reaction mixture in an amount of from about 0.01 to 4 mole percent, preferably 0.1 to 1.0 mole percent, based on the cyanide salt. Known catalysts for the reaction of alkyl isothiocyanates with alcohols include metallic acetyl acetonates such as ferric acetyl acetonate and dialkyl tin dicarboxylates and dibutyl tin dilaurate, which are recognized as good urethane catalysts. When used in the process of the present invention, high yields of thionocarbamate are obtained; however, the amount of catalyst required is high and a mole ratio of at least 1.5 moles of alcohol to isothiocyanate is required. Other good urethane catalysts, such as ferric chloride, potassium oleate, bismuth nitrate, and tertiary amines are poor catalysts for the thionocarbamate reaction; strong bases, such as sodium methoxide, are good catalysts but produce large amounts of impurities and are not practical.

Tetraalkyl titanates and tetraalkylzirconates have been found to be significantly better catalysts than either ferric acetyl acetonate or dibutyl tin dilaurate. At lower concentrations, especially at 1:1 mole ratio of isothiocyanate to alcohol, they provide higher yields and purity. These catalysts are therefore preferred, particularly the tetraalkyl titanates. The use of these catalysts in the reaction of the aliphatic alcohols with allyl isothiocyanates to produce N-allyl-O-alkyl thionocarbamates is disclosed in applicants' commonly assigned, copending application, Ser. No. 410,773, filed Aug. 23, 1982, the disclosure of which is incorporated herein by reference thereto.

In general any catalyst providing adequate yields of thionocarbamate may be employed providing they do not result in the production of large amounts of impurities and such catalysts have been collectively referred to herein as "urethane catalysts" for convenience with the understanding that not all catalysts traditionally useful in urethane production will be in this definition. Specifically exemplative of the class of catalysts useful in the instant invention include but are not limited to tetraalkyl titanates, tetraalkyl zirconates, metal acetyl acetonates, and dialkyl tin carboxylates. Preferred catalysts include ferric acetyl acetonate, dibutyl tin dilaurate and tetraalkyl titanates.

The tetraalkyl titanates which are useful in the invention are represented by the formula:

$$(RO)_4Ti$$

in which R is an alkyl group containing from 1 to 20 carbon atoms or an aryl group. The R groups may be the same or different. A preferred class of tetraalkyl titanates are those wherein R is alkyl of 1 to 10 carbon atoms. Especially preferred are tetrabutyl titanate, tetraisopropyl titanate, and tetra-2-ethylhexyl titanate.

The process of the invention is further described and illustrated by the following examples which are in no way limiting of the scope of the invention, but are provided for illustration purposes.

EXAMPLE 1

Preparation of N-Allyl-O-Isobutyl Thionocarbamate

A reaction kettle was charged with 1100 gallons of water and the pH was brought above 12 by the addition of 50% sodium hydroxide solution. Sodium cyanide (4900 pounds, 100 pound-moles) and octyldecyldimethylammonium chloride (Bardac 2050, 160 pounds, 0.24 pound-mole) were then added to the kettle. Sulfur (3225 pounds, 100.8 pound-moles) was added, with agitation, keeping the temperature at approximately 60° C. When all the sulfur was added, the reaction mixture was agitated for 30 minutes and then cooled to 40° C. Allyl chloride (8420 pounds, 110 pound-moles) was added to the reaction mixture rapidly and then the temperature was raised to bring the reaction mixture to a reflux. Heating was continued until the temperature reached 85° C. and thiocyanate content is less than 0.5%. Water (1500 gallons) was added to the reaction mixture and the mixture agitated for about 20 minutes. The aqueous phase was allowed to disengage from the organic phase and the aqueous phase was removed. The organic phase was then stripped in vacuo (22 in. Hg) until the temperature reached 100° C. (107 gallons of condensate collected). Analysis of the stripped product shows less than 0.05% water and a ratio of allyl isothiocyanate:allyl thiocyanate greater than 9:1.

The batch was cooled to 80° C. and the vacuum broken (with nitrogen). Isobutyl alcohol (less than 0.15% $H_2O$, 7413 pounds, 100 pound-moles) and 60 pounds (0.18 pound-mole) of tetra-n-butyl titanate were added and the reaction mixture was heated with agitation to 110° C. and stirred at that temperature for 8.5 hours. Conversion was 96%. A vacuum was then applied and excess alcohol was stripped. There was obtained 14,496 pounds (83.6% yield) of N-allyl-O-isobutyl thionocarbamate having a purity of 84%.

EXAMPLE 2

Preparation of N-Methallyl-O-Isobutyl Thionocarbamate

A solution of 37.2 grams (0.75 mole of 98.6% purity) of sodium cyanide, 0.6 gram of tetra-n-butyl ammonium bromide, and 70 ml water was treated with 24.2 grams (0.755 mole) of sulfur portionwise over a period of 30 minutes, the temperature increasing to 100°–110° C. The resulting solution of sodium thiocyanate was cooled to 40° C. and 84.7 ml (0.825 mole of 95% purity) methallyl chloride was added over 10–15 minutes and then the reaction mixture was brought to gentle reflux, the temperature increasing to 97° C. over 3 to 4 hours. Water (55 ml) was added to dissolve the sodium chloride and the reaction mixture was cooled to room temperature. The layers were separated and the excess methallyl chloride and trace amounts of water were stripped from the organic phase in vacuo (22 in. Hg) until the pot temperature reached 105° C. The methallyl isothiocyanate which remained was then treated with isobutyl alcohol (70.7 ml, 0.75 mole) and tetra-n-butyl titanate (0.3 gram) and the reaction mixture was heated to 100° C. under nitrogen. After 8 hours at 110° C., a 96.4% conversion with a purity of 83.4% was obtained. Unreacted isobutyl alcohol was stripped in vacuo (110° C. at 22 in. Hg) to give 125.8 grams (89.8%, based on NaCN) of N-methallyl-O-isobutyl thionocarbamate having a purity of 89.8%.

EXAMPLE 3

Preparation of N-Allyl-O-Methyl Thionocarbamate

A stirred solution of 70 ml water, 38.25 grams, (0.765 mole) of sodium cyanide and 0.15 gram (0.00046 mole) of tetra-n-butyl ammonium bromide was treated with 24.65 grams of sulfur portionwise over a period of 10 minutes, the temperature rising to reflux. The solution was cooled to less than 40° C. and 57.37 grams (0.75 mole) of allyl chloride was added over 20 minutes. The reaction mixture was heated to a gentle reflux, the temperature rising to 100° C. over 4 hours. After cooling to room temperature, 75 ml of water was added and the aqueous phase separated from the organic phase. The organic phase is stripped of allyl chloride and traces of water by heating in vacuo (20 in. Hg) to a temperature of 100° C. On cooling, 100 ml (2.47 moles) of methanol and 4 grams (0.011 mole) of ferric acetylacetonate were added and the mixture refluxed (70° C.) for 13 hours. Excess methanol was distilled, yielding 85 grams (86.5%) of N-allyl-O-methyl thionocarbamate.

EXAMPLE 4

Preparation of N-Allyl-O-n-Propyl Thionocarbamate

The procedure of Example 3 is followed except that n-propyl alcohol is used instead of methanol. After refluxing for 5.5 hours at 105° C., a similar yield of N-allyl-O-n-propyl thionocarbamate is obtained.

EXAMPLE 5

Preparation of N-Allyl-O-Isobutyl Thionocarbamate

A solution of 745.6 grams (15 moles) of sodium cyanide and 12 grams (0.037 mole) of tetra-n-butyl ammonium bromide in 1400 ml of water was treated with 483.3 grams (15.08 moles) of sulfur portionwise of 30–40 minutes, the temperature rising to 113° C. After stirring for 30 minutes, the solution was cooled to less than 40° C. Allyl chloride (1263 grams, 16.5 moles) was added over 15–20 minutes and the reaction mixture refluxed for 3.5 hours, the temperature reaching 90° C. At this point conversion of 99+% was obtained. Water (1100 ml) was added and the mixture cooled to 40° C. The aqueous phase was separated from the organic phase and the excess allyl chloride and trace amounts of water were stripped in vacuo (22 in. Hg) to a temperature of 100° C. Water content at this point was 0.02%. Isobutyl alcohol (1136 grams, 15 moles) and tetra-n-butyl titanate (9 grams, 0.026 mole) were added and the mixture was heated at 110° C. for 6.5 hours to a conversion of 96.1%. Unreacted isobutyl alcohol was stripped, yielding 2280 grams (87.9% yield) of N-allyl-O-isobutyl thionocarbamate having a purity of 87%.

EXAMPLE 6

Preparation of N-Allyl-O-Isobutyl Thionocarbamate

The procedure of Example 5 was followed except that 1.2 grams/mole of allyl isothiocyanate of a zirconium n-butoxide butanol complex $$(n-C_4H_9)_4Zr \cdot C_4H_9OH$$

was used. Reaction with isobutyl alcohol at 110° C. gave a 96.7% conversion after 3.5 hours and 98.4% conversion after 5.5 hours to N-allyl-O-isobutyl thionocarbamate having a purity of 86.6%.

What is claimed is:

1. A process for the preparation of N-allyl-O-alkyl thionocarbamates, comprising:
   (a) reacting, in the presence of a phase transfer catalyst, an alkali metal or ammonium cyanide, sulfur, and an allyl halide in water as the reaction solvent to produce a reaction mixture comprising an organic phase containing an allyl isothiocyanate and an aqueous phase;
   (b) separating said aqueous phase from said organic phase; and
   (c) reacting said allyl isothiocyanate with an alcohol in the presence of a catalyst useful for the production of urethanes to produce said N-allyl-O-alkyl thionocarbamate.

2. The process according to claim 1 wherein the N-allyl-O-alkyl thionocarbamate has the general structure

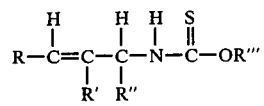

and wherein the allyl halide has the general structure

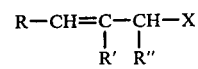

wherein R, R' and R" are individually selected from the group consisting of hydrogen, alkyl or aryl, R''' is alkyl and X is a halide.

3. The process according to claim 2 wherein at least one of the group R, R' and R" is hydrogen or an alkyl group containing one to four carbon atoms and R''' is an alkyl group containing one to eight carbon atoms.

4. The process according to claim 3 wherein R and R" are hydrogen and R' is hydrogen or methyl; R''' is a linear or branched alkyl group containing one to five carbon atoms.

5. The process according to claim 1 wherein said N-allyl-O-alkyl thionocarbamate is selected from the group consisting of N-allyl-O-isobutyl thionocarbamate; N-methallyl-O-isobutyl thionocarbamate and mixtures thereof.

6. The process according to claims 1, 2, 3, 4 or 5 wherein the reaction, in the presence of the phase transfer catalyst, of the alkali metal or ammonium cyanide, sulfur and allyl halide in water comprises the steps of:
   (a) forming an aqueous solution of said alkali metal or ammonium thiocyanate by the addition of about 0.5 to about 1.0 stoichiometric percent excess of said sulfur to an aqueous solution of said alkali metal or ammonium cyanide wherein said phase transfer catalyst is present in the amount of about 0.05 to 4 mole percent based on said alkali metal or ammonium cyanide;
   (b) adding to said thiocyanate solution at a temperature of less than about 40° C., about a 1.0 to 1.1 molar proportion based on said alkali metal or ammonium cyanide of allyl halide; and
   (c) heating the resulting reaction mixture at reflux for a period of time sufficient to achieve a ratio of allyl isothiocyanate to allylthiocyanate of at least 8.5:1.

7. The process according to claims 1, 2, 3, 4 or 5 wherein the separation of the organic phase from the aqueous phase comprises the steps of:
   (a) adding water to the reaction mixture to dissolve salt formed in the reaction;
   (b) separating the aqueous phase from the organic phase; and
   (c) removing unreacted allyl halide and trace amounts of water from said organic phase by heating said phase in vacuo for a time, temperature and vacuum sufficient to remove unreacted allyl halide and trace water.

8. The process according to claims 1, 2, 3, 4 or 5 wherein the reaction of said allyl isothiocyanate with alcohol comprises the steps of:
   (a) adding to said organic phase containing said allyl isothiocyanate about 1 to about 2 molar proportions based on said allyl isothiocyanate of a linear or branched chain primary alcohol and from about 0.1 to 4 mole percent based on said allyl isothiocyanate of a urethane catalyst; and
   (b) heating the resulting mixture to a temperature sufficient and for a time sufficient to convert said allyl isothiocyanate to N-allyl-O-alkyl thionocarbamate.

9. The process according to claim 8 wherein said urethane catalyst is selected from the group consisting of tetraalkyl titanates, tetraalkyl zirconates, metal acetylacetonates, and dialkyl tin dicarboxylates.

10. The process according to claim 9 further comprising recovering the N-allyl-O-alkyl thiocarbamate by in vacuo distillation of unreacted alcohol.

11. The process according to claim 9 wherein said temperature is about 100° C. to about 120° C.

12. A process for the preparation of N-allyl-O-alkyl thionocarbamates comprising:
   (a) forming an aqueous solution of an alkali metal or ammonium thiocyanate by the addition of about 0.5 to 1.0 stoichiometric percent excess of sulfur to an aqueous solution of an alkali metal or ammonium cyanide in the presence of about 0.05 to 4 mole percent based on said alkali metal or ammonium cyanide of a phase transfer catalyst;
   (b) adding to said thiocyanate solution at a temperature of less than about 40° C., about a 1.0 to 1.1 molar proportion based on said alkali metal or ammonium cyanide, of allyl halide;
   (c) heating the resulting reacton mixture at reflux for a period of time sufficient to achieve a ratio of allyl isothiocyanate to allylthiocyanate of at least 8.5:1;
   (d) adding water to the reaction mixture to dissolve salt formed in the reaction;
   (e) separating the aqueous phase from the organic phase;
   (f) removing unreacted allyl halide and trace amounts of water from said organic phase by heating said phase in vacuo for a time, temperature, and vacuum sufficient to remove unreacted allyl halide and trace water;
   (g) adding to said organic phase containing said allyl isothiocyanate about 1 to about 2 molar proportions based on said allyl isothiocyanate of a linear or branched chain primary alcohol and from about 0.1 to 4 mole percent based on said allyl isothiocyanate of a urethane catalyst; and
   (h) heating the resulting mixture to a temperature sufficient and for a time sufficient to convert said allyl isothiocyanate to N-allyl-O-alkyl thiocarbamate.

13. The process according to claim 12 wherein said urethane catalyst is selected from the group consisting of tetraalkyl titanates, tetraalkyl zirconates, metal acetyl acetonates, and dialkyl tin carboxylates.

14. The process according to claims 1, 2, 3, 4, 5, 12 or 13 wherein said phase transfer catalyst is used in an amount of about 0.1 to 1.0 mole percent based on the weight of said alkali metal or ammonium cyanide.

15. The process according to claims 1, 2, 3, 4, 5, 12 or 13 wherein said urethane catalyst is used in an amount of about 0.1 to 1.0 mole percent based on said alkali metal or ammonium cyanide.

16. The process according to claim 15 wherein said urethane catalyst is a tetraalkyl titanate.

17. The process according to claim 16 wherein said tetraalkyl titanate is tetra-n-butyl titanate.

* * * * *